United States Patent
Long et al.

(10) Patent No.: US 11,241,585 B2
(45) Date of Patent: *Feb. 8, 2022

(54) METHOD AND APPARATUS FOR REMOVABLE CATHETER VISUAL LIGHT THERAPEUTIC SYSTEM

(71) Applicant: LIGHT LINE MEDICAL, INC., Salt Lake City, UT (US)

(72) Inventors: Curtis D. Long, Cottonwood Heights, UT (US); Mitchell D. Barneck, Clearfield, UT (US); Nathaniel L. Rhodes, Salt Lake City, UT (US); James P. Allen, Salt Lake City, UT (US); Martin de la Presa, Salt Lake City, UT (US)

(73) Assignee: Light Line Medical, Inc., Salt Lake City, UT (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/747,315

(22) Filed: Jan. 20, 2020

(65) Prior Publication Data

US 2020/0147406 A1    May 14, 2020

Related U.S. Application Data

(63) Continuation-in-part of application No. 15/424,732, filed on Feb. 3, 2017, now Pat. No. 10,543,338.

(60) Provisional application No. 62/292,028, filed on Feb. 5, 2016.

(51) Int. Cl.
*A61N 5/06* (2006.01)
*A61M 25/01* (2006.01)
*A61N 5/067* (2006.01)

(52) U.S. Cl.
CPC ....... *A61N 5/0601* (2013.01); *A61M 25/0108* (2013.01); *A61N 5/062* (2013.01);
(Continued)

(58) Field of Classification Search
CPC .............. A61M 25/0108; A61M 39/10; A61M 39/105; A61N 2005/0602;
(Continued)

(56) References Cited

U.S. PATENT DOCUMENTS

| | | |
|---|---|---|
| 5,053,003 A | 10/1991 | Dadson et al. |
| 5,855,203 A | 1/1999 | Matter |

(Continued)

FOREIGN PATENT DOCUMENTS

| | | |
|---|---|---|
| WO | WO2006/074509 | 7/2006 |
| WO | WO2019/027478 | 2/2019 |

*Primary Examiner* — Jonathan T Kuo
(74) *Attorney, Agent, or Firm* — Madson IP, P.C.

(57) ABSTRACT

A medical device assembly is provided for removable insertion into a catheter with a lumen. The medical device assembly comprises an electromagnetic radiation (EMR) source for providing non-ultraviolet, therapeutic EMR having an intensity sufficient to inactivate one or more infectious agents and/or to stimulate healthy cell growth causing a healing effect, and a removable EMR conduction system at least partially insertable into and removable from the lumen of the catheter. The EMR conduction system has at least one optical element providing axial propagation of the therapeutic EMR through an insertable elongate body. The elongate body may have an exterior surface between a coupling end and a distal end tip that has at least one modified portion permitting the radial emission of therapeutic EMR from the elongate body proximate the modified portion. Such modified portion may be gradient along the exterior surface.

20 Claims, 11 Drawing Sheets

(52) U.S. Cl.
CPC ............ *A61N 5/0624* (2013.01); *A61N 5/067* (2021.08); *A61N 2005/063* (2013.01); *A61N 2005/0629* (2013.01); *A61N 2005/0651* (2013.01); *A61N 2005/0662* (2013.01)

(58) Field of Classification Search
CPC ...... A61N 2005/0629; A61N 2005/063; A61N 2005/0651; A61N 2005/0662; A61N 2005/067; A61N 5/0601; A61N 5/062; A61N 5/0624; A61N 5/06–2005/073
See application file for complete search history.

(56) References Cited

U.S. PATENT DOCUMENTS

| | | | |
|---|---|---|---|
| 9,808,647 B2* | 11/2017 | Rhodes | ............... A61N 5/0624 |
| 10,543,338 B2* | 1/2020 | Barneck | ............... A61M 25/00 |
| 2004/0193218 A1 | 9/2004 | Butler | |
| 2007/0260295 A1 | 11/2007 | Chen et al. | |
| 2008/0051736 A1 | 2/2008 | Rioux et al. | |
| 2009/0048648 A1 | 2/2009 | Dacey, Jr. et al. | |
| 2011/0208274 A1 | 8/2011 | Bornstein | |
| 2011/0295343 A1 | 12/2011 | Bornstein et al. | |
| 2012/0321509 A1 | 12/2012 | Bak | |
| 2013/0267888 A1 | 10/2013 | Rhodes et al. | |
| 2013/0303996 A1 | 11/2013 | Rasooly et al. | |
| 2014/0235942 A1 | 8/2014 | Hellstrom et al. | |
| 2015/0057648 A1 | 2/2015 | Swift et al. | |
| 2015/0231287 A1 | 8/2015 | Lin et al. | |
| 2015/0297767 A1 | 10/2015 | Gaska et al. | |
| 2016/0279402 A1 | 9/2016 | Stigall et al. | |
| 2018/0015302 A1 | 1/2018 | Barneck et al. | |
| 2018/0178029 A1 | 6/2018 | Rogers et al. | |
| 2019/0217117 A1 | 7/2019 | Barneck et al. | |
| 2019/0358387 A1 | 11/2019 | Elbadry et al. | |

* cited by examiner

METHOD AND APPARATUS FOR REMOVABLE CATHETER VISUAL LIGHT THERAPEUTIC SYSTEM

RELATED APPLICATION

This application is a continuation-in-part of U.S. patent application Ser. No. 15/424,732, filed on Feb. 3, 2017 and entitled METHODS AND APPARATUS FOR REMOVABLE CATHETER VISUAL LIGHT THERAPEUTIC SYSTEM and claims the benefit of U.S. Provisional Patent Application, Ser. No. 62/292,028 that was filed on Feb. 5, 2016, for an invention titled METHOD AND APPARATUS FOR REMOVABLE CATHETER VISUAL LIGHT STERILIZATION SYSTEM, each of which is incorporated herein by this reference, as if fully set forth herein.

BACKGROUND OF THE INVENTION

Field of the Invention

The present invention is a method and apparatus to provide therapeutic doses of non-ultraviolet light to inactivate infectious agents residing on, within, or generally around a catheter while the catheter is residing within a body cavity and/or to stimulate healthy cell growth causing a healing effect. In particular, the disclosure is a medical device assembly that utilizes non-ultraviolet visual therapeutic electromagnetic radiation (EMR) at a high enough intensity to stimulate healthy cell growth causing a healing effect and/or to reduce or eliminate infectious agents in, on, and around a catheter while it resides inside a body cavity.

Various exemplary embodiments of the present invention are described below. Use of the term "exemplary" means illustrative or by way of example only, and any reference herein to "the invention" is not intended to restrict or limit the invention to exact features or steps of any one or more of the exemplary embodiments disclosed in the present specification. References to "exemplary embodiment," "one embodiment," "an embodiment," "some embodiments," "various embodiments," and the like, may indicate that the embodiment(s) of the invention so described may include a particular feature, structure, or characteristic, but not every embodiment necessarily includes the particular feature, structure, or characteristic. Further, repeated use of the phrase "in one embodiment," or "in an exemplary embodiment," do not necessarily refer to the same embodiment, although they may.

The Relevant Technology

Catheters are used commonly as channels to inject medications into or retrieve fluid samples from a patient. Each catheter comprises a tube, usually made from plastic or other polymers, such as silicone, polyurethane, and the like, that is inserted into an area of the body and may contain one or more separate lumens through which fluids may be delivered or retrieved. A "lumen" designates an enclosed pathway within the catheter that goes from outside the body to inside the body. Catheters are used in various applications, including intravascularly, urologically, gastrointestinally, ophthalmically, within the respiratory tract, within the cranium, and the like. In all cases, the catheter may be placed inside of a space in the body where the catheter resides, herein referred to as a "body cavity". These devices frequently give rise to infections caused by growth of infectious agents in, on, and around the catheter. Infectious agents can include bacteria, fungi, viruses, or the like that enter the body and lead to illness of the patient. Depending on the location of the catheter placement, these infections can arise in the form of urinary tract infections, blood stream infections, soft tissue infection, and the like.

Catheter related infections (CRIs) are a large problem in medicine, leading to high morbidity and mortality rates. Current methods for reducing or eliminating the number of infectious agents in and on a catheter are of low efficacy. Typically, catheters may be removed if they are suspected to be harboring infectious agents, increasing both the cost associated with treatment and patient discomfort. Various methods to deter or eliminate growth of infectious agents in catheters have been attempted such as using sterile handling techniques, antibiotics, and replacing the catheter when an infection is suspected. Despite these techniques, infections resulting from catheters remain a major problem. According to the Centers for Disease Control and Prevention, over 31,000 people died specifically from catheter-related bloodstream infections in 2010. These infections, along with urinary tract infections, gastrointestinal infections, and other infections from catheters, increase both medical costs and patient discomfort.

Catheters come in various sizes. Those that are smaller in diameter, such as many PICC lines (peripherally inserted central catheters), have small diameter lumens. Such smaller diameter catheters may be suitable for prolonged insertion. Consequently, with smaller diameter catheters, there may be inadequate thickness to the catheter wall to carry a sterilization delivery system.

Accordingly, there exists a need for a method and apparatus designed to deliver non-antibiotic, bactericidal therapeutics in-vivo. Such a method and apparatus, using novel technology, may provide removable delivery of safe, effective, and reproducible disinfection.

SUMMARY OF THE INVENTION

The exemplary embodiments of the present disclosure comprise methods and apparatuses for inactivating infectious agents and/or stimulating healthy cell growth causing a healing effect on, around, and in connection with catheters. In particular, the methods utilize removably insertable apparatuses for this inactivation and/or healing to occur while the catheter is residing within a patient's body cavity. Generally, this disclosure addresses a medical device assembly for removable insertion into a lumen within the catheter. The medical device assembly comprises an electromagnetic radiation (EMR) source, a removable EMR conduction system, and at least one coupling to connect the radiation source to the EMR conduction system. The EMR source provides non-ultraviolet, therapeutic EMR having intensity sufficient to inactivate one or more infectious agents and/or to stimulate healthy cell growth causing a healing effect. The removable EMR conduction system is at least partially insertable into and removable from the lumen of the catheter.

The EMR source can be from a single or group of EMR sources including, but not limited to, a light emitting diode, a semiconductor laser, a diode laser, an incandescent (filtered or unfiltered) and a fluorescent (filtered or unfiltered) light source. This EMR source provides non-ultraviolet, therapeutic EMR providing one or more wavelengths in the range of above 380 nm to about 900 nm. In order to provide sufficient inactivation of infectious species and/or stimulation of healthy cell growth, each EMR wavelength should be of a narrow spectrum and centered around one wavelength from the group. The intensity should be sufficient to inactivate one or more infectious agents and/or to stimulate healthy cell growth causing a healing effect. This group includes several wavelengths: 400 nm, 405 nm, 415 nm, 430 nm, 440 nm, 445 nm, 455 nm, 470 nm, 475 nm, 632 nm, 632.8 nm, 640 nm, 650 nm, 660 nm, 670 nm, 680 nm, 780 nm, 808 nm, 830 nm, and 904 nm.

The EMR source may require drivers and electronic support for full functionality. Consideration should be given to accommodating the support hardware and/or software, which may encompass a significant portion of the EMR source's functionality and efficacy. It is possible that the EMR source may generate heat, which could be detrimental to the EMR source and may need to be limited.

One exemplary embodiment of the EMR source and support components is simplified to contain only the EMR source and necessary components. In another exemplary embodiment of the EMR conduction system, a passive heat sink is required to diffuse the heat generated into the surrounding environment. In yet another exemplary embodiment of the EMR source, a heat sink may be couple to at least one fan to actively dissipate heat generated by the EMR source.

Of particular interest to this disclosure is the use of light between 380 nm and about 900 nm wavelengths. Additionally, the intensity and power of the light emitted bear significantly on the inactivation of infectious agents, thus a range of radiant exposures covering 0.1 J/cm$^2$ to 1 kJ/cm$^2$ and a range of powers from 0.005 mW to 1 W, and power density range covering 1 mW/cm$^2$ and 1 W/cm$^2$ are of interest for these exemplary device assemblies and methods. These ranges of wavelengths, power densities, and radiant exposures have been shown to have either antimicrobial effects or positive biological effects on healing tissue. These positive biological effects include reduction of inflammatory cells, increased proliferation of fibroblasts, stimulation of collagen synthesis, angiogenesis inducement and granulation tissue formation.

For each exemplary embodiment described herein, the EMR conduction system and method for disinfection/healing could be utilized in an adjustable or predetermined duty cycle. If treatments began immediately after sterile procedure was initiated, device related infections may be inhibited. This includes device related biofilm growth.

For the purposes of this disclosure the use of the term "duty cycle" should be understood to mean of or relating to the delivery of non-ultraviolet visual, therapeutic EMR by at least one of a single, multiple, variable, continuous, indefinite, increasing-intensity lead-in, decreasing-intensity phase-out, or any combination thereof on-and-off period of EMR dosing via the EMR conduction system of this disclosure.

A treatment may include at least one wavelength of therapeutic EMR that acts as a predominant wavelength selected to sterilize one or more target organisms and selected from the group of wavelengths centered about 400 nm, 405 nm, 415 nm, 430 nm, 440 nm, 445 nm, 455 nm, 470 nm, 475 nm, 660 nm, and 808 nm. Or, a predominant wavelength selected to promote healing and healthy cell growth may be selected from the group of wavelengths centered about 632 nm, 632.8 nm, 640 nm, 650 nm, 660 nm, 670 nm, 680 nm, 780 nm, 808 nm, 830 nm, and 904 nm. Another treatment may include alternating the predominant wavelength between a first predominant wavelength and a second predominant wavelength (differing from the first predominant wavelength) in a selected treatment pattern.

Further, sterilizing EMR and EMR that stimulates healthy cell growth may be transmitted simultaneously in tandem or alternatively.

The removably insertable EMR conduction system may comprise at least one optical element having an elongate body conducive to the axial propagation of the therapeutic EMR through the elongate body. This elongate body may have an exterior surface between a coupling end and a distal end tip. The exterior surface may have at least one modified portion wherein the modified portion permits the radial emission of therapeutic EMR from the elongate body proximate the modified portion.

The at least one coupling to connect the radiation source to the EMR conduction system may comprise at least one feature that allows for the coupling to be readily removable from the removable EMR conduction system. This coupling may be achieved by utilizing a uniquely designed connection, a pre-manufactured coupling system, or any combination thereof that optimizes the coupling efficiency and utility. Further, the coupling that couples the removably insertable EMR conduction system to the EMR source may comprise more than one coupling with an intermediate section optimized to further the propagation of the EMR. In one exemplary embodiment, the EMR source is coupled to a patch cable or EMR conduction extending segment, which is then coupled to the formal removably insertable EMR conduction system.

For the purposes of this disclosure the use of the term "therapeutic" should be understood to mean of or relating to the treatment of disease, including reducing or eliminating infectious agents, as well as serving or performed to maintain health, including enhancing healthy cell growth.

The optical element further comprises at least one optical feature selected from a group of optical features such as a reflective surface, an optically transmissible material, a lens, a fiber optic filament, and any combination thereof. The optical element also may be capable of transmitting more than one wavelength or intensity EMR. Multiple wavelengths may be transmitted simultaneously, one after another or in tandem, or a combination thereof (for example, one constantly on and the other wavelength pulsed). Multiple intensities may be transmitted through the same element simultaneously. Alternating patterns of light treatments may also be transmitted.

The EMR conduction system may be configured to insert, at least partially, into one of any number of catheters, such as by way of example only and not to be limiting: a central venous catheter, a peripheral insertion catheter, a peripheral insertion central catheter, a midline catheter, a jugular catheter, a subclavian catheter, a femoral catheter, a cardiac catheter, a cardiovascular catheter, a urinary Foley catheter, an intermittent urinary catheter, an endotracheal tube, a gastrointestinal catheter, a nasogastric tube, a wound drainage catheter, or any similar accessing medical catheter or tube that has been inserted into a patient for the purpose of delivering or retrieving fluids or samples.

One exemplary embodiment of the EMR conduction system has an optical element comprising a single, insertable optical fiber. With a single optical fiber, the single fiber may allow light to transmit radially or axially at various sections along its length. For sections where light will transmit radially, the exterior surface of the optical element may be modified by chemical etching, physical etching, or electromagnetic ablation through plasma or lasers to modify various sections along the length of the optical fiber. The modified portions permit light to emit radially.

For purposes of this disclosure, light emitted radially means that the light has a radial component. Hence, the light emitted radially may emit perpendicularly and/or obliquely to the central axis of the optical fiber at the axial point of emission.

For embodiments having modified sections, the material comprising the optical fiber may be selected from a group of materials comprising optical fibers including plastic, silica, fluoride glass, phosphate glass, chalcogenide glass, plastic, and any other suitable material that is capable of axial light propogation and surface modification to achieve radial emission. In addition, the optical fibers may be single mode, multi-mode, or plastic optical fibers that may have been optimized for modification using a chemical, physical, or electromagnetic manufacturing modification process. The optical fibers may also be optimized for modification post-production.

Yet another exemplary embodiment employs a physical abrasion method of alteration to modify the EMR conduction system comprised of at least one optical fiber. This fiber would be utilized based on its optimal optical response to the physical abrasion process. This process may include, but is not limited to, sanding, media blasting, grinding, buffing, or media blasting at least one section of the optical fiber. The physical abrasion process would also necessarily be optimized in terms of the extent of physical abrasion to optimize the appropriate radial EMR emission or lack thereof. This may be accomplished by adjusting at least one of velocity, acceleration, pressure, modification time, or abrasion material utilized in modifying the optical fiber.

Yet another exemplary embodiment employs microscopic porous structures in the optical fiber to achieve radial transmission of light. These microscopic structures may be positioned within the core and/or core-cladding boundary of the optical fiber. The microscopic structures having a refractive index lower than the region free of microscopic structures. The microscopic structures may be a material added to the optical fiber core or the core-cladding boundary, such as a metal, rubber, or plastic. The microscopic structures may also be the lack of material creating an aberration within the optical fiber core or the core-cladding boundary. For example, the presence of microscopic bubbles in the optical fiber core would create an aberration or imperfection that would alter the materials refractive index, resulting in EMR being radially emitted from the optical fiber.

Another exemplary embodiment may comprise at least one optical fiber with cladding modified to optimize the radial or axial propagation of EMR. For example, the cladding may be modified to at least partially remove or thin the cladding in order to achieve partial radial transmission of EMR. Another example could include an optical fiber with only certain portions containing cladding, the EMR transmitting axially in the clad portions and at least partially axially and radially in the non-clad portions.

Yet another exemplary embodiment achieves radial transmission equivalency wherein the radially emitting portion of the optical fiber has substantially equivalent intensity over the length of the emitting portion along the optical fiber. This may be done through chemical etching, physical etching, plasma ablation, or laser ablation in a gradient pattern. By altering at least one of velocity, acceleration, pressure gradients, flow, modification time, or modification material or process, it is possible to achieve radial transmission equivalency throughout each portion or the entire length of the modified optical fiber. During manufacturing, a gradient-provided equivalency also may be achieved through addition of microscopic structures positioned within the core and/or core-cladding boundary in a gradient pattern. Also, radial transmission equivalency achieved through gradient cladding or core features are contemplated for achieving desired radial emission, whether substantially equivalent over a portion length or varying as desired.

Still another exemplary embodiment achieves a gradient radial transmission wherein at least one portion of the optical fiber emits EMR radially in a gradient distribution. The gradient distribution may also be accomplished through chemical etching, physical etching, plasma or laser ablation in a uniform or gradient pattern. By altering at least one of velocity, acceleration, pressure gradients, flow, modification time, or modification material or process, it is possible to achieve a gradient radial transmission throughout a portion of modified optical fiber. This may also be achieved through addition of microscopic structures positioned within the core and/or core-cladding boundary.

A further exemplary embodiment of the removable EMR conduction system comprises an optical element such as at least one LED, its associated wiring components, and a scaffold. The LED(s) may emit EMR based on the LED's inherent distribution, or may utilize another optical element, such as a lens or mirror, to focus or diffuse the EMR in the direction of interest. In addition, more than one LED could be arranged in an array to appropriately emit EMR for maximal therapeutic benefit. The LED(s), together with associated wiring components may be permanently or removably attached to the scaffold, which allows for removable insertion of the EMR conduction system into a catheter. The scaffold may be rigid, semi-rigid, malleable, elastic, or flexible, or any combination thereof.

Another exemplary embodiment comprises a plurality of optical elements where the lumen is sufficiently large to receive a plurality of optical elements. The elongate body of each optical element has a length and at least two of the elongate bodies may have differing lengths such that elongate bodies of differing lengths terminate at varying distances from the coupling end of the elongate body. Additionally, where in-lumen space permitting, multiple optical elements of various lengths may be arranged to achieve a gradient distribution pattern and/or multiple emitting portions.

For each exemplary embodiment, the assembly and method for disinfection may be utilized in an adjustable or predetermined duty cycle or duty cycles. If treatments begin immediately after sterile procedure has been initiated, device-related infections may be inhibited. Also, if treatments begin after device-related infection(s) have been detected, the treatment may cause the inactivation of one or more infectious agents. It should be understood that inactivating infectious agents includes inhibiting infectious agents and infectious agents includes device-related biofilm growth.

BRIEF DESCRIPTION OF THE DRAWINGS

In order that the manner in which the above-recited and other features and advantages of the present disclosure are obtained will be readily understood, reference is made to exemplary embodiments thereof which are illustrated in the appended figures. Understanding that these figures depict only typical exemplary embodiments and are not therefore to be considered limiting of the scope of the present disclosure, the exemplary embodiments will be described and explained through the use of the accompanying figures in which.

REFERENCE NUMERALS

Figure 1:
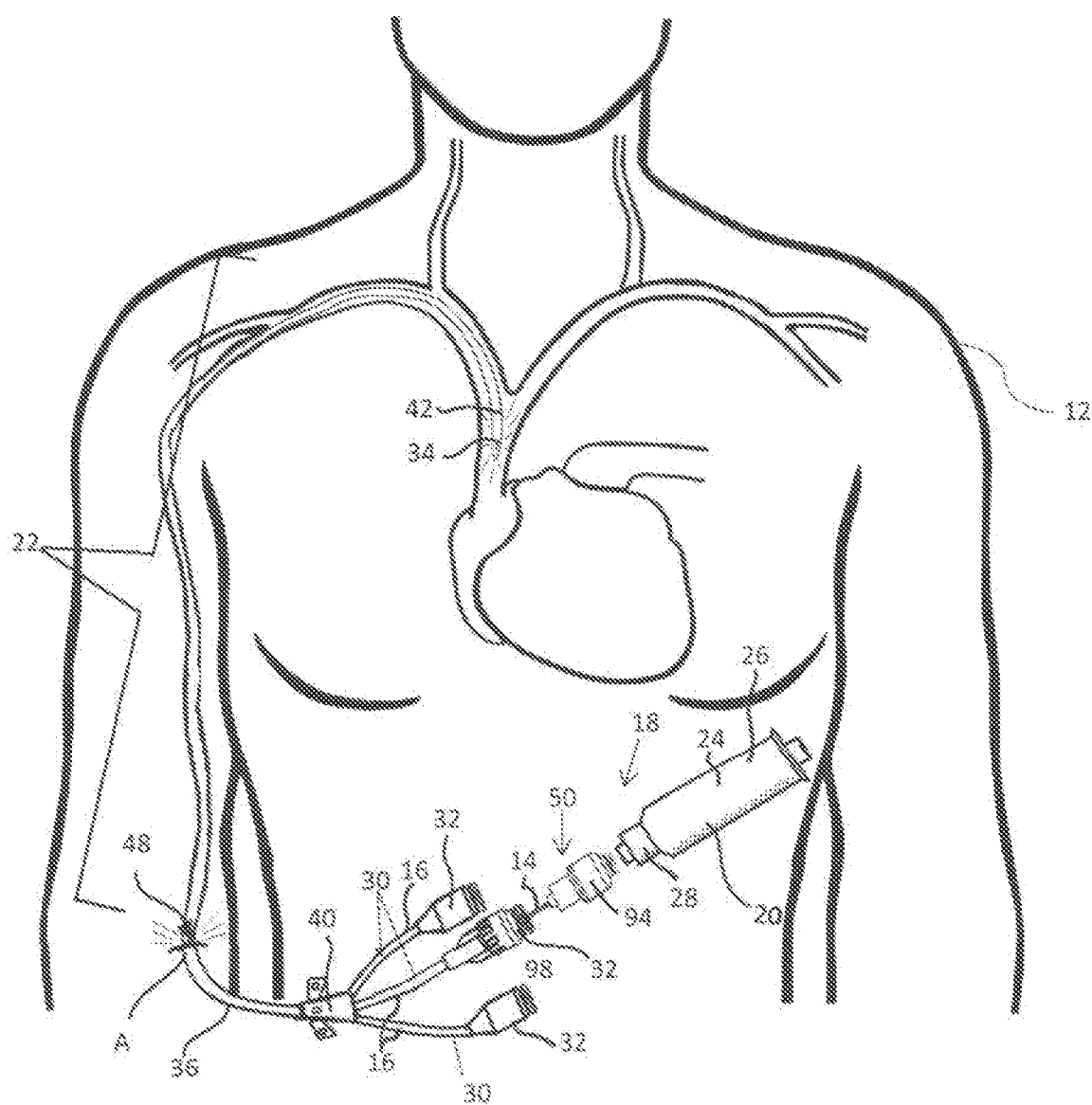
FIG. 1 is a schematic view of a triple lumen catheter, an insertable optical element, and an EMR component.

| | |
|---|---|
| catheter 10 | patient's body 12 |
| insertable optical element 14 | line tubing 16 |
| EMR conduction system 18 | electromagnetic radiation component 20 |
| insertable catheter component 22 | elongate body 24 |
| electromagnetic radiation power source 26 | coupling element 28 |
| internal lumen 30 | |
| distal end tip 34 | proximal catheter hub assembly 32 |
| catheter of varying lengths 38 | elongate catheter body 36 |
| termination of the optical element 42 | convergence chamber 40 |
| line clamp 46 | flexible protection tubing 44 |
| optical assembly 50 | transdermal area 48 |
| patch cable 54 | intermediate coupling 52 |
| forward connector 58 | EMR conduction extending segment 56 |
| exterior surface 62 | rearward connector 60 |
| connecting element 88 | tip 64 |
| collimating lens 92 | EMR hub connector 90 |
| alignment shaft 98 | optical element connector 94 |
| non-modified optical span 100 | an aligning bore 99 |
| single modified portion 103 | segment-modified optical span 102 |
| single elongated modified portion 105 | fully-modified optical span 104 |
| modified tip portion 107 | multi-modified optical span 106 |
| microscopic structures free area 109 | first section 108 |
| minimal concentration 111 | second section 110 |
| moderate concentration 113 | third section 112 |
| maximal concentration 115 | fourth section 114 |
| microscopic structures 117 | core 116 |
| cladding boundary 120 | optical element cladding 118 |
| control device 122 | first dispersal 121 |
| wand 124 | second dispersal 123 |
| acid spray 126 | third dispersal 125 |
| inner region 129 | outer region 127 |
| insertion site A | boundary region 131 |

DETAILED DESCRIPTION OF THE INVENTION

The exemplary embodiments of the present disclosure will be best understood by reference to the drawings, wherein like parts are designated by like numerals throughout. It should be understood that the components of the exemplary embodiments, as generally described and illustrated in the figures herein, could be arranged and designed in a wide variety of different configurations. Thus, the following more detailed description of the exemplary embodiments of the apparatus, system, and method of the present disclosure, as represented in FIGS. 1 through 11, is not intended to limit the scope of the invention, as claimed, but is merely representative of exemplary embodiments.

In this application, the phrases "connected to", "coupled to", and "in communication with" refer to any form of interaction between two or more entities, including mechanical, capillary, electrical, magnetic, electromagnetic, pneumatic, hydraulic, fluidic, and thermal interactions.

The phrases "attached to", "secured to", and "mounted to" refer to a form of mechanical coupling that restricts relative translation or rotation between the attached, secured, or mounted objects, respectively. The phrase "slidably attached to" refer to a form of mechanical coupling that permits relative translation, respectively, while restricting other relative motions. The phrase "attached directly to" refers to a form of securement in which the secured items are in direct contact and retained in that state of securement.

The term "abutting" refers to items that are in direct physical contact with each other, although the items may not be attached together. The term "grip" refers to items that are in direct physical contact with one of the items firmly holding the other. The term "integrally formed" refers to a body that is manufactured as a single piece, without requiring the assembly of constituent elements. Multiple elements may be formed integral with each other, when attached directly to each other to form a single work piece. Thus, elements that are "coupled to" each other may be formed together as a single piece.

FIG. 1 of the present disclosure depicts a schematic view of an exemplary triple lumen catheter 10 with the catheter 10 shown disposed within a patient's body 12. An insertable optical element 14 is inserted partially into the catheter 10, and an EMR component 20 is connected to the insertable optical element 14.

The catheters 10 depicted in FIGS. 1-4 are exemplary multiple lumen catheters 10 each also comprises line tubing 16, one or more (in FIG. 1, three are shown, in FIGS. 2-4, two are shown) proximal catheter hub assemblies 32, an elongate catheter body 36, a distal end tip 34, and a convergence chamber 40. Internal lumen 30 has an inner diameter (i.e., an interior surface dimension) and runs the length of the catheter 10, from the proximal catheter hub assembly 32, through the line tubing 16, the convergence chamber 40, and the elongate catheter body 36, to the distal end tip 34. The insertable optical element 14 is elongate with an outer diameter (i.e., an exterior surface dimension) sufficiently small to be insertable within at least one of the internal lumens 30 and may extend at least as far into the catheter 10 as a termination of the optical element 42, although the insertion may be less than that length if desired.

Catheters 10 suitable for use with the insertable optical element 14 may be of several different makes, sizes, and functions. For example, catheters that are translucent may be particularly suited to permit the passage of radially emitted EMR therethrough to the tissue surrounding the catheter 10.

Catheters 10 that have an interior surface dimension (inside diameter) sufficiently larger than the exterior surface dimension (outer diameter) of the insertable optical element 14 may permit the injection or withdrawal of fluid (liquid or gas) simultaneously through the catheter while that insertable optical element 14 resides within the catheter 10.

Also, some catheters 10 have radiopacifiers embedded within the walls of the catheter 10 so that an image of where the catheter 10 is located within the patient's body 12 may be determined. However, some catheters have no such radiopacifiers. In either case, it is contemplated by this disclosure that radiopacifiers may be contained in or on the insertable optical element 14 to provide detection of the location of the catheter 10 within the patient's body 12 when the catheter 10 does not have radiopacifiers, and to provide detection of the location of the insertable optical element 14 disposed within the catheter 10 whether or not the catheter 10 has radiopacifiers (this may require differing radiopacifiers in some instances so that the catheter 10 and the insertable optical element 14 may be distinguished).

With some exemplary embodiments, at least one of the proximal catheter hub assemblies 32 may have an optical fiber element alignment shaft 98 that aligns an optical element connector 94 and the insertable optical element 14.

FIG. 1 shows the catheter 10, in a schematic view, inserted at an insertion site A in an arm of the patient's body 12. The depiction shows how non-ultraviolet, therapeutic EMR may be delivered at the insertion site A and to other sites within the patient's body 12. At the insertion site A, the therapeutic EMR may be delivered to a transdermal area 48 to inactivate infectious agents in that area and to enhance healing of the insert site A. Similarly, proximate the distal end tip 34, in this case within the vena cava, therapeutic EMR may be delivered to inactivate infectious agents and/or to enhance healing in that proximate vicinity.

The EMR component 20 comprises the EMR power source 26 (FIGS. 2-4), a light source (not shown, such as a laser or the like), electrical circuitry (not shown), and optics (not shown, but dependent upon the light source) all housed within an elongate body 24. A coupling element 28 connects the EMR component 20 to an optical assembly 50. The optical assembly 50 comprises the insertable optical element 14 and the optical element connector 94. The combination of the EMR component 20, the coupling element 28, and the optical assembly 50, comprising the insertable optical element connector 94 and the insertable optical element 14, will be referred to herein as a removable EMR conduction system 18.

Of particular interest to each of the embodiments is the use of light having wavelengths ranging from above 380 nm and about 900 nm. Additionally, the intensity and power of the light emitted server to inactivate of infectious agents and/or to promote healing. A range of radiant exposures covering 0.1 J/cm$^2$ to 1 kJ/cm$^2$ and a range of powers from 0.005 mW to 1 W, and power density range covering 1 mW/cm$^2$ and 1 W/cm$^2$ are of interest for these exemplary device assemblies and methods. These ranges of wavelengths, power densities, and radiant exposures have been shown to have either antimicrobial effects or positive biological effects on healing tissue. These positive biological effects include reduction of inflammatory cells, increased proliferation of fibroblasts, stimulation of collagen synthesis, angiogenesis inducement and granulation tissue formation.

For each exemplary embodiment described herein, the EMR conduction system 18 and method for disinfecting/healing could be utilized in an adjustable or predetermined duty cycle or duty cycles. If treatments began immediately after sterile procedure was initiated, device-related infections may be inhibited. Also, if treatments begin after device-related infection(s) have been detected, the treatment may cause the inactivation of one or more infectious agents. It should be understood that inactivating infectious agents includes inhibiting infectious agents and infectious agents includes device-related biofilm growth.

An exemplary adjustable, predetermined duty cycle may effectively utilize at least one of a power ranging from 0.005 mW to 1 W, a power density from a range covering 1 mW/cm$^2$ and 1 W/cm$^2$ and radiant exposure from a range covering 0.1 J/cm$^2$ to 1 kJ/cm$^2$ and at least one of a single, multiple, variable, continuous, indefinite, increasing-intensity lead-in, decreasing-intensity phase-out, or any combination thereof on-and-off periods. EMR dosing uses the EMR conduction system of this disclosure and operated in duty cycles.

Infectious agents may include but are not limited to bacteria, fungi, viruses, and protozoa that invade the body and lead to or cause illness of the patient. Depending on the application, infectious agents vary by type and sensitivity to EMR inactivation. Effective duty cycles and EMR dosing may be standardly optimized by those skilled in the art through empirical derivation. Through such empirical derivation, effective duty cycles may be identified whereby duty cycle intensity causes a therapeutic effect of at least one of inactivating one or more infectious agents and promoting healing.

One exemplary application of interest pertains to catheters utilized in environments subjected to continuous contamination from infectious agents. In this exemplary application one effective duty cycle (on-and-off period) is repeated continuously for the effective life of the catheter. Treatments composed of multiple effective duty cycles each with intensity sufficient to inactivate one or more infectious agents may inhibitor eradicate device-related infections and/or device-related biofilm growth.

Another exemplary duty cycle may include the EMR conduction system delivering EMR with an intensity sufficient to inactivate one or more infectious agents and/or to stimulate healthy cell growth causing a healing effect by utilizing an "on" period of 120 minutes followed by an "off" period of 10 minutes. This on-and-off pattern may be repeated continuously for 30 days providing sterilizing and/or healing EMR for the effective life of the catheter.

The foregoing being only representative examples, it should be understood that a duty cycle(s) is/are adjustable and may be comprised of an unlimited number of possible combinations of at least one of a power ranging from 0.005 mW to 1 W, a power density from a range covering 1 mW/cm$^2$ and 1 W/cm$^2$ and a radiant exposure from a range covering 0.1 J/cm$^2$ to 1 kJ/cm$^2$ and at least one of a single, multiple, variable, continuous, indefinite, increasing-intensity lead-in, decreasing-intensity phase-out, or any combination of on-and-off period(s). On-and-off periods may comprise of at least one of an infinite combination of nanoseconds, milliseconds, seconds, minutes, hours, or days.

A treatment may include at least one wavelength of therapeutic EMR that acts as a predominant wavelength selected to sterilize one or more target organisms and selected from the group of wavelengths centered about 400 nm, 405 nm, 415 nm, 430 nm, 440 nm, 455 nm, 470 nm, 475 nm, 660 nm, and 808 nm. Another treatment may include alternating the predominant wavelength between a first predominant wavelength and a second predominant wavelength (differing from the first predominant wavelength) in a selected treatment pattern. Further, sterilizing EMR and EMR that stimulates healthy cell growth may be transmitted simultaneously in tandem or alternatively.

Figure 2:
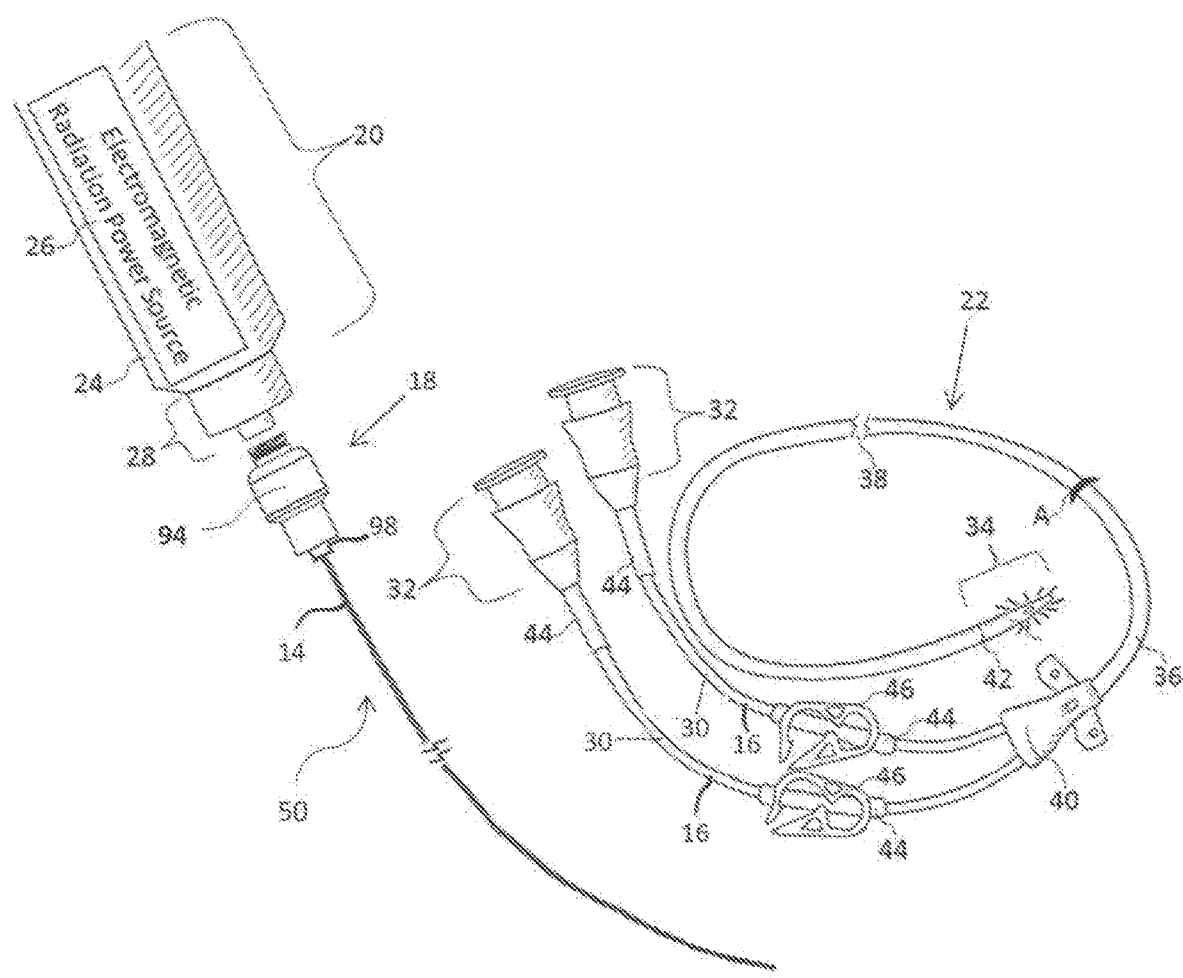
FIG. 2 is a perspective view of a dual lumen catheter with the insertable component outside the catheter.

Another embodiment of the present disclosure is depicted in FIG. 2, showing a perspective view of a dual lumen catheter 10 with the removable EMR conduction system 18 outside the catheter 10. The catheter 10 portion of the depiction shows flexible protection tubing 44 that protects the coupling of the proximal catheter hub assembly 32 with the line tubing 16 and also protects line tubing 16 from wear imposed by line clamps 46.

Figure 3:
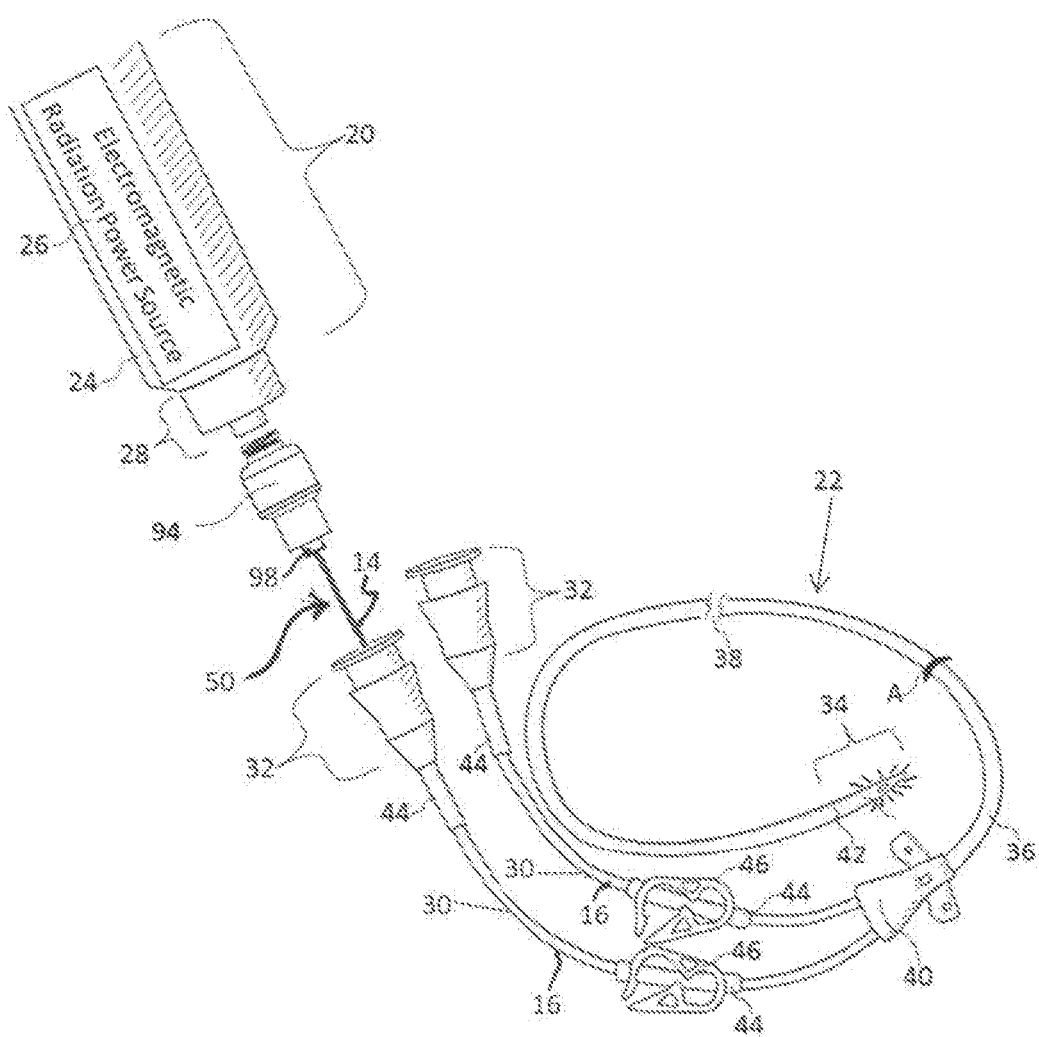
FIG. 3 is a perspective view of a dual lumen catheter with the insertable component disposed partially inside the catheter.

FIG. 3 shows the dual lumen catheter 10 of FIG. 2 with the removably insertable EMR conduction system 18 partially inserted into one of the lumens 30 of the catheter 10.

Figure 4:
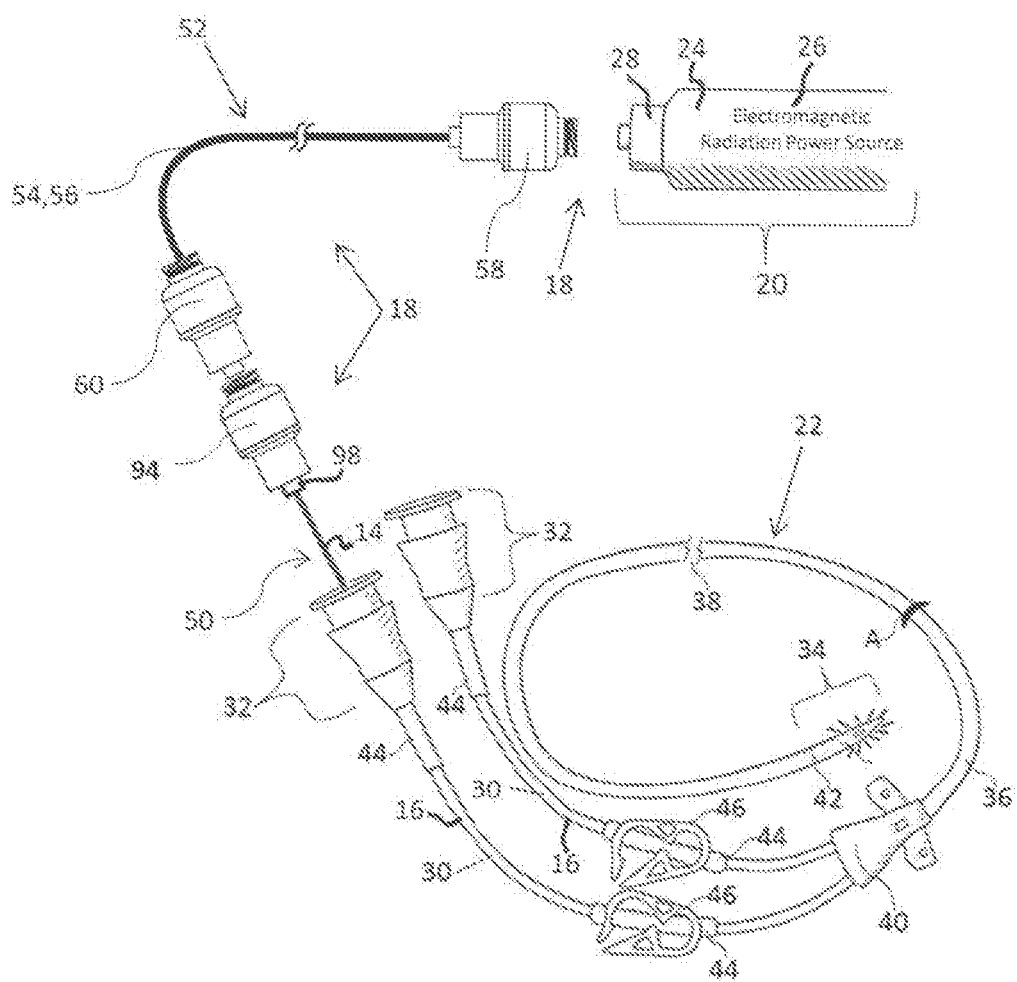
FIG. 4 is a perspective, partially exploded view of a dual lumen catheter with the insertable component disposed partially inside the catheter and showing an intermediate coupling.

FIG. 4 shows an exploded perspective view of an exemplary EMR conduction system 18 as partially inserted into the proximal catheter hub assembly 32 and an internal lumen 30. With this exemplary embodiment, an intermediate coupling 52 is shown. Such intermediate coupling 52 may comprise a patch cable 54 or an EMR conduction extending segment 56 used to extend the distance between the EMR power source 26 and the optical element connector 94 of the insertable optical element 14, without appreciable loss of light intensity. Each of the patch cable 54 or EMR conduction extending segment 56 may have a forward connector 58 to securely engage coupling element 28, and a rearward connector 60 to securely engage the optical element connector 94. Hence, by using a patch cable 54 or an EMR conduction extending segment 56, the EMR power source 26 may be operated some desired distance from the patient to reduce noise or heat concerns and/or to position the EMR power source 26 closer to a power source (not shown) such as an electrical outlet or battery pack.

Figure 5:
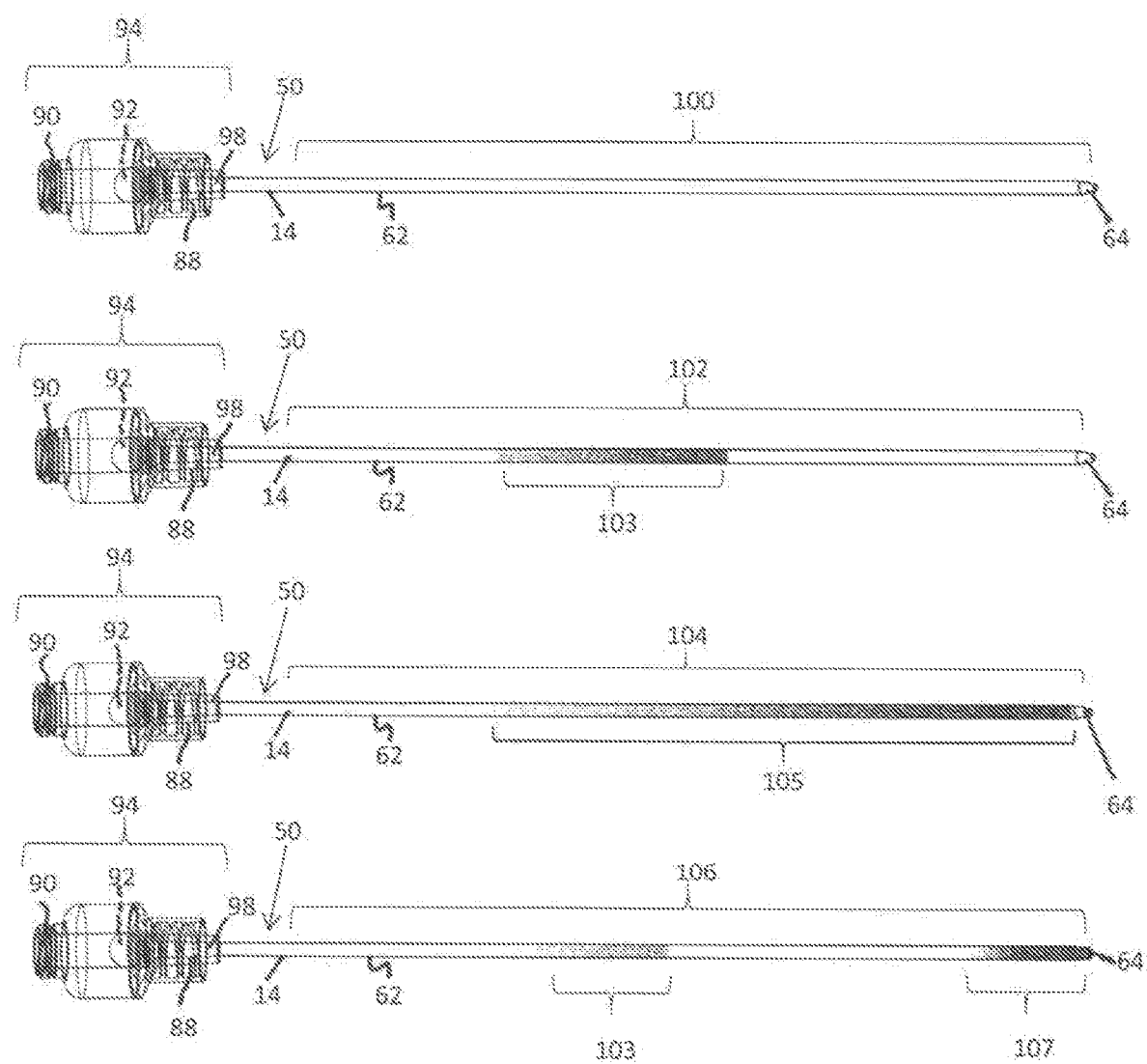
FIG. 5 is a series of elevation views of several exemplary embodiments of an insertable optical element with varying locations, lengths, and degrees of modification, and with the optical element connector shown as transparent.

FIG. 5 is a series of elevation views of several exemplary embodiments of an optical assembly 50 showing various locations with gradient degrees of modification on the exterior surface 62 of the insertable optical element 14. Each view of the series of views shows an optical assembly 50 with an insertable optical element 14 connected to the optical element connector 94. The optical element connector 94 (see also FIG. 10) has a connecting element 88, an EMR hub connection 90, a collimating lens 92, and an alignment shaft 98.

The first view (uppermost) of the series of views shows a non-modified optical span 100 of the insertable optical element 14 that is without any radial dispersion (i.e., the insertable optical element 14 has not been modified to provide radial emission of light from the body of the insertable optical element 14). With this embodiment, therapeutic, non-ultra-violet EMR may be provided to a tip 64 with no radial emission from the non-modified optical span 100 other than at the tip 64.

The second view (next view down) of the series of views shows an exemplary radial transmission equivalency over a single modified portion 103 (i.e., modified portion 103 has a gradient modification such that the emitted light has substantially the same intensity and power over the length of the modified portion 103) that provides radially dispersed light from a segment-modified optical span 102. The location of the single modified portion 103, in this instance, corresponds to where the catheter 10 enters the insertion site A when the insertable optical element 14 is inserted fully into the catheter 10. With this embodiment, radially emitted visual light may sterilize the insertion site A and the transdermal area 48 or any other predetermined site within the patient's body 12.

The third view of the series of views shows an example of a single elongated modified portion 105 that provides radially dispersed light from optical element 14 extending along most of a fully-modified optical span 104. The location of the single elongated modified portion 105 corresponds generally to the length of the insertable catheter component 22 of the catheter 10. With this embodiment, therapeutic light may be provided for substantially the entire length that the catheter 10 would be inserted within the patient's body 12.

The fourth view of the series of views shows an example of radial transmission equivalency at multiple locations. A single modified portion 103 and an additional radial transmission equivalency at a modified tip portion 107 are spaced along a multi-modified optical span 106. The locations of the modified portion 103 and the modified tip portion 107 correspond to areas of the body, including for example the insertion site A, where the delivery of non-ultraviolet, therapeutic EMR may be desired for sterilization and/or healing. It should be understood that there may be more than one modified portion 103 disposed along the length of the multi-modified optical span 106 and/or each modified portion 103 may have various lengths.

Also, it should be understood that in each of these views the modified portions depicted may be of modifications other than modification of the exterior surface 62 of the insertable optical element 14, such as for example, modifications including microscopic structures embedded within the insertable optical element 14 that allow radial transmission of light from the insertable optical element 14. Further, such modified portions 103, 105, 107 may have gradient patterns that allow for an overall substantially-uniform distribution of light over the length of the modified portion 103, 105, 107.

Figure 6:
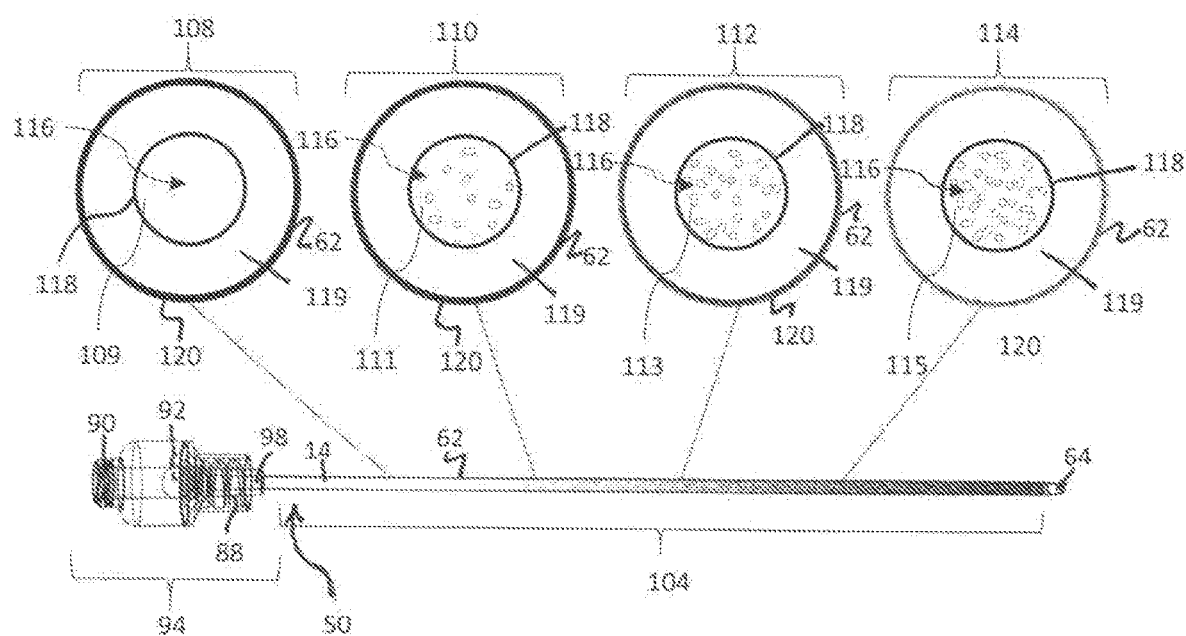
FIG. 6 shows cross-sectional views of multiple portions of an insertable optical element with various EMR radial, gradient dispersion levels.

FIG. 6 is a schematic view of an optical assembly 50 with an insertable optical element 14 coupled to an optical element connector 94. The insertable optical element 14 has a fully-modified optical span 104. Multiple locations along the insertable optical element 14 are shown in enlarged cross-sectional views. These locations are axially spaced along the insertable optical element 14 to assist in describing the nature of an exemplary insertable optical element 14 at each location. As depicted, there are four section locations, a first section 108, a second section 110, a third section 112, and a fourth section 114. For brevity, the modifications on and in the insertable optical element 14 at each of the four sections are combined in the depictions of FIG. 6. Of course, the modified portion of the insertable optical element 14 may be singular or multiple, may be any length or gradient, and may be coincident, overlapping or not.

The first section 108 represents an internally reflected region of the insertable optical element 14. As shown at the first section 108, there is no ablation (or other modification) and no microscopic structure within the core 116 of the insertable optical element 14. No therapeutic non-ultra-violet EMR will emit radially from the insertable optical element 14 at the first section 108.

The second section 110 represents a minimally emissive region of the insertable optical element 14. As shown at the second section 110, there is minimal ablation (or other modification) to the exterior surface 62 of the insertable optical element 14 and a minimal dispersal of microscopic structures 117 within the core 116 of the insertable optical element 14. From the second section 110, minimal therapeutic, non-ultra-violet EMR will emit radially from the insertable optical element 14. However, the amount of EMR emitted should have sufficient intensity and power to inactivate infectious agents and/or promote healing proximate the second section 110.

The third section 112 represents a moderately emissive region of the insertable optical element 14. As shown at the third section 112, there is moderate ablation (or other modification) to the exterior surface 62 of the insertable optical element 14 and moderate dispersal of microscopic structures 117 within the core 116 of the insertable optical element 14. From the third section 112, a moderate amount of therapeutic, non-ultra-violet EMR will emit radially from the insertable optical element 14 proximate the third section 112. However, prior to reaching the third section 112, the amount of light traveling down the insertable optical element 14 diminishes due to the radial emission of some of the light such as at second section 110. Consequently, the degree of the gradient of modification is selected so that the amount of EMR emitted radially at third section 112 should be substantially equivalent to the radial emission at the second section 110. Hence, the intensity and power of the EMR emitted may be substantially equivalent to the intensity and power emitted at second section 110 and is of sufficient intensity and power to inactivate infectious agents and/or promote healing.

The fourth section 114 represents a maximally emissive region of the insertable optical element 14. As shown at the fourth section 114, there is maximal ablation (or other modification) to the exterior surface 62 of the insertable optical element 14 and maximal dispersal of microscopic structures 117 within the core 116 of the insertable optical element 14. From the fourth section 114, a maximum amount of therapeutic, non-ultra-violet EMR will emit radially from the insertable optical element 14 proximate the fourth section 114. Again, prior to reaching the fourth section 114, the amount of light continuing to travel down the insertable optical element 14 diminishes due to the radial emission of some of the light such as at second section 110 and at third section 112. Consequently, the degree of the gradient of modification is selected so that the amount of EMR emitted radially at fourth section 114 should be substantially equivalent to the emissions at second section 110 and third section 112. The intensity and power of the EMR emitted may be substantially equivalent to the intensity and power emitted at second section 110 and third section 112 and is of sufficient intensity and power to inactivate infectious agents and/or promote healing.

The modified portions may be modified by chemical, physical or other cladding modification (e.g., ablation) to alter the critical angle enough to allow light to emit radially. Additionally or alternatively, the modified portions may be modified by dispersing microscopic structures 117 of varying gradient concentration inside the core 116 of the insertable element 14. The gradient concentration of microscopic structures 117 within the core 116 shown in FIG. 6 range from a microscopic structures free area 109, to a minimal concentration 111 of microscopic structures 117, to a moderate concentration 113 of microscopic structures 117, to a maximal concentration 115 of microscopic structures 117.

The concentration of microscopic structures 117 within the core 116 affects the refractive index of the core 116 and the core-cladding boundary 118. The microscopic structures 117 (which may be voids, such as bubbles) create changes in the incident angle of the light as it passes through the insertable optical element 14. At certain incident angles, light leaves the optical element cladding 119 and emits radially from the cladding boundary 120.

Figure 7:
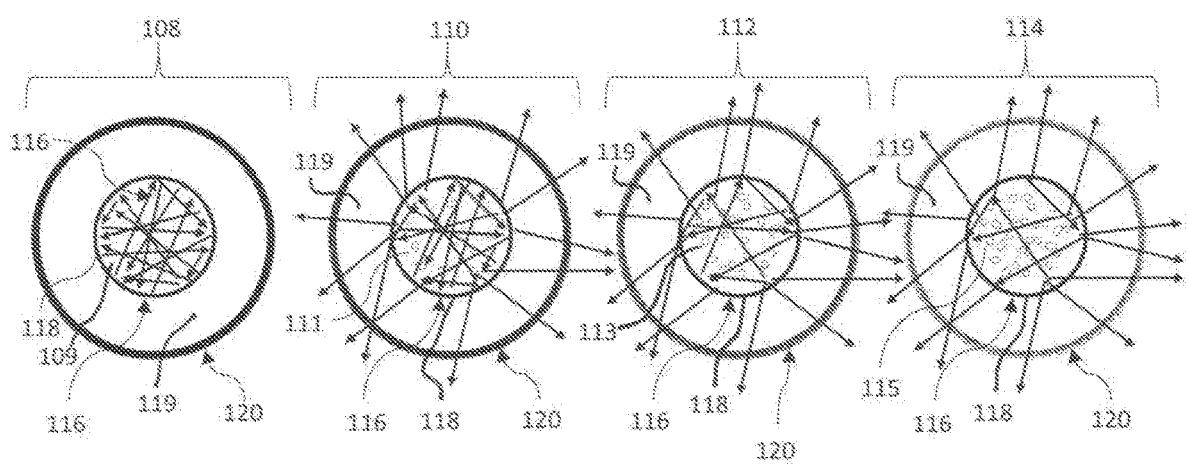
FIG. 7 shows the cross-sectional views of various gradient dispersion levels of FIG. 6 showing the sections with EMR ray diagrams of internal reflection, and relative radial emission.

FIG. 7 is a schematic view of the cross-sectional views of FIG. 6 depicting light rays as arrows. The same cross-sectional views of the insertable optical element 14 are shown: namely, the first section 108 (internally reflected), the second section 110 (minimally radially emissive), the third section 112 (moderately radially emissive), and the fourth section 114 (maximally radially emissive). These views also show light rays traveling down the core 116, that collide with microscopic structures 117 at an incident angle causing the light ray to pass through the optical element cladding 119. An increasing pixilated gradient is depicted on the cladding boundary 120 from the first section 108 (no pixilation), to the second section 110 (minimal pixilation), to the third section 112 (moderate pixilation), to the fourth section 114 (maximal pixilation) represents the chemical, physical or other cladding modification (e.g., ablation) at the cladding boundary 120. Such modification of the insertable optical element 14 alters critical angles enough to allow light to emit radially. As schematically depicted, the amount of rays leaving the optical element cladding 119 are substantially equivalent at each site although the amount of rays the core 116 diminishes as the light travels from proximal to distal. The microscopic structures 117 of varying gradient concentration are also shown inside the core 116, from the microscopic structure free area 109, to a minimal concentration 111, to a moderate concentration 113, to a maximal concentration 115. Each of the microscopic structures 117 has a refractive index that differs from that of the core 116 and the optical element cladding 119. The microscopic structures 117 (which may be voids, such as bubbles) create changes in the incident angle of the light as it passes through the insertable optical element 14. At certain incident angles, light leaves the optical element cladding 119 and emits radially.

Figure 8:
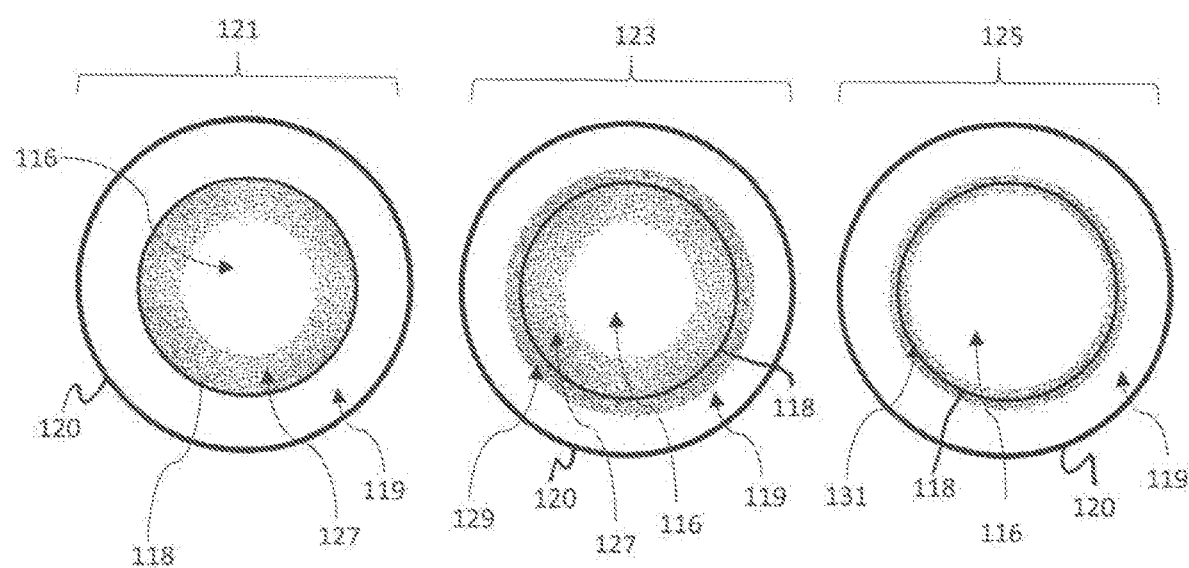
FIG. 8 shows cross-sectional views of various exemplary dispersals of microscopic structures (such as flecks or bubbles) within a fiber optic's core, cladding, and the core/cladding boundary.

FIG. 8 shows cross-sectional views of various exemplary dispersals of microscopic structures 117 (such as flecks or bubbles) within a fiber optic's core 116, cladding 119, and the core/cladding boundary 118. With each of the exemplary embodiments depicted microscopic structures 117 are dispersed within the insertable optical element 14 (in this case an optical fiber) to achieve radial transmission of light. These microscopic structures 117 may be positioned within the core 116 and/or at the core-cladding boundary 118 and/or within the cladding 119 of the optical fiber 14. The microscopic structures 117 having a refractive index lower than the region free of microscopic structures 117. The microscopic structures 117 may be a material added to the optical fiber core 116 or the core-cladding boundary 118, such as a metal, rubber, or plastic. The microscopic structures 117 may also be the lack of material creating an aberration within the optical fiber core 116 and/or the core-cladding boundary 118 and/or within the cladding. For example, the presence of microscopic structures 117 (such as bubbles) in the optical fiber core 116 creates an aberration or imperfection that would alter the materials refractive index, resulting in EMR being emitted radially from the optical fiber (insertable optical element 14).

In FIG. 8, three exemplary dispersals, a first dispersal 121, a second dispersal 123, and a third dispersal 125, are depicted. The first dispersal 121 has microscopic structures 117 (such as flecks or bubbles) dispersed within and outer region 127 of the core 116 only. The second dispersal 123 has microscopic structures 117 dispersed within an inner region 129 of the cladding 119 as well as within the outer region 127 of the core 116. The third dispersal 125 has microscopic structures 117 dispersed proximate to the core/cladding boundary 118 and are depicted as identifying a boundary region 131 that is thinner than the outer region 127 of the core 116 and the inner region 129 of the cladding 119. With each of these exemplary dispersals, at least some of the light traveling the length of the insertable optical element 14 (fiber optic) will not encounter any microscopic structures 117 while the remainder of the light may encounter at least one microscopic structure 117 and be deflected to emit radially from the insertable optical element 14.

Figure 9:
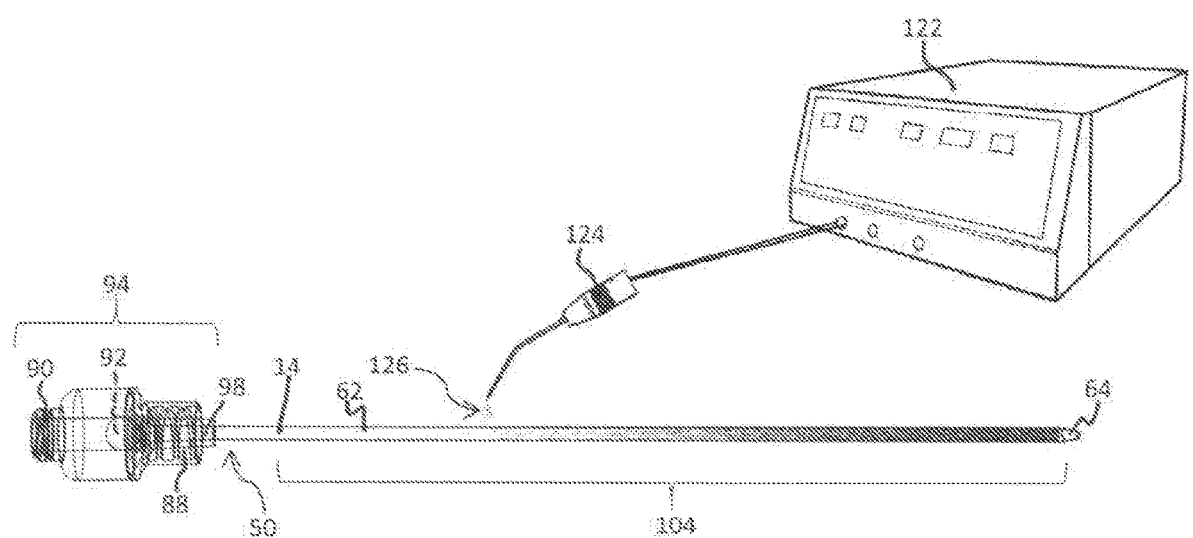
FIG. 9 is a schematic view of a treatment being applied to the insertable optical element.

FIG. 9 is a schematic view of an exemplary optical element modification method for creating gradient modification on the exterior surface 62 of the insertable optical element 14. Such modification of the core 116 or optical element cladding 118 alters the incident angle of light rays so that they differ from the critical angle needed to remain internally reflected. Depicted in FIG. 9 is a control device 122 with a wand 124 delivering an acid spray 126 for etching the insertable optical element 14.

There are several methods for achieving this gradient modification. Chemically, the insertable optical element 14 may be etched using a strong acid such as hydrofluoric acid or sulfuric acid and hydrogen-peroxide. Also, quartz powder, calcium fluoride, or an etching cream, usually carrying a fluorinated compound, may be used. Physically, heating the insertable optical element 14 or physical modification such as ablation by sanding, media blasting, grinding, or laser ablation modifications are also methods for creating gradient modification. Additionally, plasma ablation by laser modification causes the ionization of molecules and alteration of the exterior surface 62 of the insertable optical element 14. Other known methods for creating gradient ablation are contemplated by this disclosure. Regardless of the modification or manufacturing process, whether presently known or not, the insertable optical element 14 may be modified to have substantially equivalent radially emitted light along desired lengths. This uniformity in radially emitted light allows for a more accurate treatment dose for inactivating infectious agents and/or promoting healing.

Figure 10:
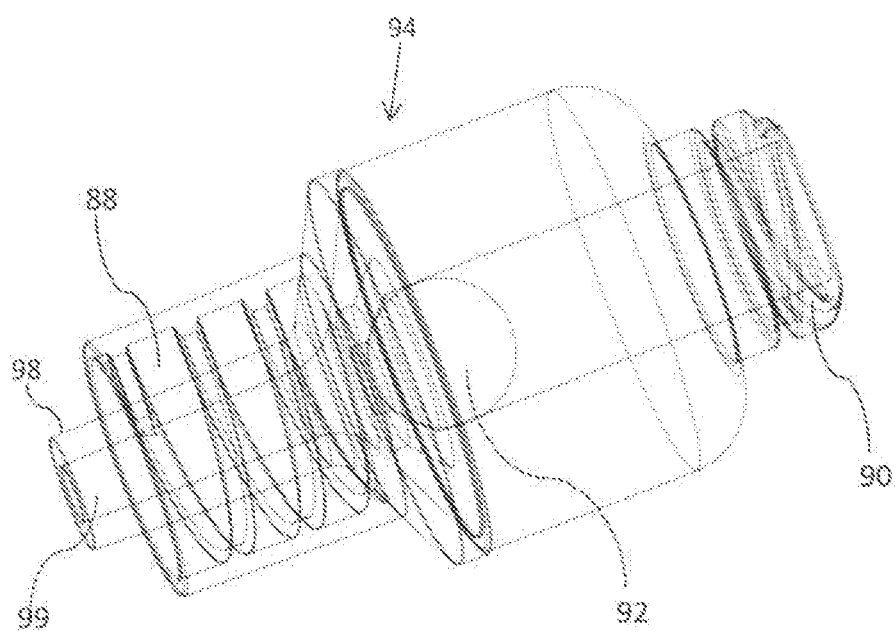
FIG. 10 is a perspective, transparent view of an optical element connector showing an exemplary optical collimating element.

In FIG. 10 of the present disclosure, a transparent view of the optical element connector 94 is depicted, comprising a connecting element 88, an EMR hub connection 90, a collimating lens 92, an alignment shaft 98, and an aligning bore 99. The insertable optical element 14 may be inserted into the aligning bore 99 of the optical element connector 94 to collimate the light into a small diameter core 116 or one or more optical fibers.

The exemplary disclosure depicts an optical diversion element as a single collimating lens 92, but other types of optical diversion elements such as multiple lenses or different types of lenses may be used to collimate the light. Depending on the optical element 14 diameter, numerical aperture, and refractive index, specific lenses will be needed as an optical diversion element to reduce light loss.

Figure 11:
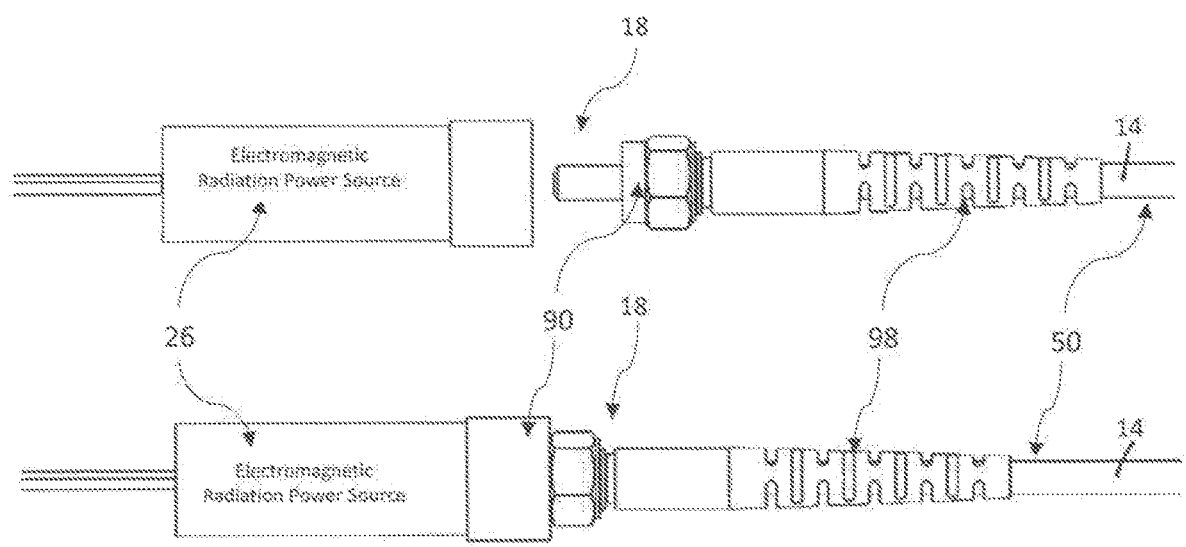
FIG. 11 shows plan views of an optical element assembly and EMR power source, detached and attached, which does not require a collimating lens.

Referring now to FIG. 11 of the present disclosure, depicted are a pair of EMR conduction systems 18, one in exploded view and one in assembled view, each EMR conduction system has an EMR power source 26 that is attachable to an optical assembly 50 having an optical element connector 94 without a collimating lens 92. In instances where the numerical aperture, diameter, and material can be matched with that of the optical element 14, a collimating lens 92 may not be required. In such instances the EMR hub connector 90 may connect directly to the EMR power source 26 and the optical element connector 94, as depicted.

This disclosure anticipates that the system and methods of this disclosure may be embodied in other specific forms without departing from its structures, methods, or other essential characteristics as broadly described herein and claimed hereinafter. The described embodiments are to be considered in all respects only as illustrative, and not restrictive. The scope of the disclosure is, therefore, indicated by the appended claims, rather than by the foregoing description. All changes that come within the meaning and range of equivalency of the claims are to be embraced within their scope.

For exemplary methods or processes of the invention, the sequence and/or arrangement of steps described herein are illustrative and not restrictive. Accordingly, it should be understood that, although steps of various processes or methods may be shown and described as being in a sequence or temporal arrangement, the steps of any such processes or methods are not limited to being carried out in any particular sequence or arrangement, absent an indication otherwise. Indeed, the steps in such processes or methods generally may be carried out in various different sequences and arrangements while still falling within the scope of the present invention.

Additionally, any references to advantages, benefits, unexpected results, or operability of the present invention are not intended as an affirmation that the invention has been previously reduced to practice or that any testing has been performed. Likewise, unless stated otherwise, use of verbs in the past tense (present perfect or preterit) is not intended to indicate or imply that the invention has been previously reduced to practice or that any testing has been performed.

Exemplary embodiments of the present invention are described above. No element, act, or instruction used in this description should be construed as important, necessary, critical, or essential to the invention unless explicitly described as such. Although several exemplary embodiments have been described in detail herein, those skilled in the art will readily appreciate that many modifications are possible in these exemplary embodiments without materially departing from the novel teachings and advantages of this invention. Accordingly, all such modifications are intended to be included within the scope of this invention as defined in the appended claims.

In the claims, any means-plus-function clauses are intended to cover the structures described herein as performing the recited function and not only structural equivalents, but also equivalent structures. Thus, although a nail and a screw may not be structural equivalents in that a nail employs a cylindrical surface to secure wooden parts together, whereas a screw employs a helical surface, in the environment of fastening wooden parts, a nail and a screw may be equivalent structures. Unless the exact language "means for" (performing a particular function or step) is recited in the claims, a construction under Section 112, 6th paragraph is not intended. Additionally, it is not intended that the scope of patent protection afforded the present invention be defined by reading into any claim a limitation found herein that does not explicitly appear in the claim itself.

What is claimed is:

1. A medical device assembly for delivering electromagnetic radiation (EMR) into, onto, and around a catheter indwelling within a patient's body and having at least one lumen, the medical device assembly comprising:

an EMR source for providing non-ultraviolet, therapeutic EMR having an intensity comprising at least one of a radiant exposure of at least 0.5 J/cm$^2$ and up to 1 kJ/cm$^2$, power of at least 0.005 mW and up to 1 W, and power density of at least 0.1 mW/cm$^2$ and up to 1 W/cm$^2$, whereby such intensity causes a therapeutic effect of at least one of inactivating one or more infectious agents and promoting healing;

an EMR conduction system comprising an optical element connector and an optical element having an elongate body and a distal end tip, at least a portion of the optical element being insertable into a disposition within and removable from the lumen of the catheter while the catheter resides within the patient's body, the elongate body being conducive to the axial propagation of the non-ultraviolet, therapeutic EMR through the elongate body, the elongate body having an exterior surface between a proximal coupling end and the distal end tip, the exterior surface having at least one radial emission portion between the proximal coupling end and the distal end tip allowing the emission of non-ultraviolet, therapeutic EMR radially from the elongate body into the lumen of the catheter and through the catheter, thereby delivering a duty cycle of the non-ultraviolet, therapeutic EMR into, onto, and around the catheter while the optical element resides in the disposition and the catheter resides within the patient's body, the duty cycle comprising at least one of a single, multiple, variable, continuous, increasing-intensity lead-in, decreasing-intensity phase-out, and any combination thereof on-and-off periods; and a coupling to connect the EMR source to the optical element connector of the EMR conduction system and to deliver the non-ultraviolet, therapeutic EMR from the EMR source to the optical element for axial propagation of the non-ultraviolet, therapeutic EMR through the elongate body.

2. The medical device assembly as in claim 1 wherein the optical element further comprises at least one optical feature selected from a group of optical features consisting of a reflective surface, an optically transmissible material, a lens, a fiber optic filament, and any combination thereof.

3. The medical device assembly as in claim 1 wherein the medical device assembly is configured to deliver sterilizing EMR and healing EMR alternatively, alternatingly, or simultaneously.

4. The medical device assembly as in claim 1 further comprising at least one optical diversion element to redirect the non-ultraviolet, therapeutic EMR from at least one of the EMR source and the optical element into at least one fluid line, a convergence chamber, and a catheter connection hub.

5. The medical device assembly as in claim 1 wherein the non-ultraviolet, therapeutic EMR has a wavelength that ranges from above 380 nm to 900 nm.

6. The medical device assembly as in claim 1 wherein the duty cycle length is adjustable.

7. The medical device assembly as in claim 1 wherein the EMR source is selected from a group consisting of a solid-state laser, a semiconductor laser, a diode laser, a light emitting diode, a fluorescent, or an incandescent light source.

8. The medical device assembly as in claim 1, wherein the delivery of a duty cycle of the non-ultraviolet, therapeutic EMR around the catheter comprises delivery of non-ultraviolet, therapeutic EMR into tissue proximate to the catheter.

9. The medical device assembly as in claim 1, wherein the on-and-off periods of the duty cycle comprise at least one of any combination of nanoseconds, milliseconds, seconds, minutes, hours, and days.

10. The medical device assembly as in claim 1 wherein at least a portion of the emission of the non-ultraviolet, therapeutic EMR is emitted to sterilize a portion of the medical device assembly outside the patient's body.

11. The medical device assembly as in claim 1 wherein the therapeutic effect is inactivating one or more infectious agents and the radial emission of the non-ultraviolet, therapeutic EMR is onto the catheter comprises inhibiting device-related biofilm growth.

12. A medical system for delivering electromagnetic radiation (EMR) into a patient's body, medical system comprising:

a catheter having at least one lumen;

a medical device assembly for delivering (EMR) into, onto, and around the catheter:

an EMR source for providing non-ultraviolet, therapeutic EMR having a wavelength in a range of above 380 nm to 904 nm and having an intensity comprising at least one of a radiant exposure of at least 0.5 J/cm$^2$ and up to 1 kJ/cm$^2$, power of at least 0.005 mW and up to 1 W, and power density of at least 0.1 mW/cm$^2$ and up to 1 W/cm$^2$, whereby such intensity causes a therapeutic effect of at least one of inactivating infectious agents and promoting healing;

an EMR conduction system comprising at least one optical element having an elongate body conducive to the axial propagation of the non-ultraviolet, therapeutic EMR along the elongate body, at least one of the optical elements being at least partially insertable into and removable from at least one of the lumen of the catheter while the catheter resides within the patient's body, the non-ultraviolet, therapeutic EMR emitting radially from the elongate body into the lumen and through the catheter, thereby delivering a duty cycle of the non-ultraviolet, therapeutic EMR into, onto, and around the catheter while the catheter resides within the patient's body, the duty cycle comprising at least one of a single, multiple, variable, continuous, increasing-intensity lead-in, decreasing-intensity phase-out, and any combination thereof on-and-off periods; and at least one coupling to connect the EMR source to the EMR conduction system and to deliver the non-ultraviolet, therapeutic EMR from the EMR source to the optical element for axial propagation of the non-ultraviolet, therapeutic EMR through the elongate body.

13. The medical system as in claim 12 wherein the wavelength of the non-ultraviolet, therapeutic EMR is selected from a group of wavelengths consisting of wavelengths centered about 400 nm, 405 nm, 415 nm, 430 nm, 440 nm, 445 nm, 455 nm, 470 nm, 475 nm, 632 nm, 632.8 nm, 640 nm, 650 nm, 660 nm, 670 nm, 680 nm, 780 nm, 808 nm, 830 nm, and 904 nm.

14. The medical system as in claim 12 wherein the non-ultraviolet, therapeutic EMR comprises one or more of the selected wavelengths being emitted in at least one of alternating and parallel treatment patterns.

15. The medical system as in claim 12 wherein the optical element has an exterior surface dimension less than an interior surface dimension of the lumen such that a liquid may be injected into or withdrawn from the lumen between the interior surface dimension of the lumen and the exterior surface dimension of the optical element while the optical element resides within the catheter.

16. The medical system as in claim 12 wherein the therapeutic effect is inactivating one or more infectious agents and the radial emission of the non-ultraviolet, therapeutic EMR is onto the catheter comprises inhibiting device-related biofilm growth.

17. A method for effectively delivering non-ultraviolet, therapeutic EMR into a catheter while the catheter is indwelling within a patient's body, the catheter having a lumen with an interior surface dimension, comprising the steps of:
- inserting an optical element of an EMR conduction system into a disposition within the lumen of the catheter, the optical element having an exterior surface dimension which is less than the interior surface dimension of the lumen such that the optical element is removably insertable into the lumen of the catheter;
- transmitting a duty cycle of non-ultraviolet, therapeutic EMR from an EMR source into the optical element of the EMR conduction system for an amount of time and at an intensity comprising at least one of a radiant exposure of at least 0.5 J/cm$^2$ and up to 1 kJ/cm$^2$, power of at least 0.005 mW and up to 1 W, and power density of at least 0.1 mW/cm$^2$ and up to 1 W/cm$^2$, whereby such intensity causes a therapeutic effect of at least one of inactivating one or more infectious agents and promoting healing;
- emitting the duty cycle of non-ultraviolet, therapeutic EMR radially into the lumen of the catheter and through the catheter, the duty cycle comprising at least one of a single, multiple, variable, continuous, increasing-intensity lead-in, decreasing-intensity phase-out, and any combination thereof on-and-off periods;
- delivering the duty cycle of the non-ultraviolet, therapeutic EMR into, onto, and around the catheter while the optical element resides in the disposition and the catheter resides within the patient's body; and
- removing the optical element of the EMR conduction system from the lumen of the catheter, the catheter remaining indwelling within the patient's body.

18. The method of claim 17 wherein the catheter permits the non-ultraviolet, therapeutic EMR to transmit into tissue surrounding the catheter within the patient's body.

19. The method of claim 17 wherein at least a portion of the emission of the non-ultraviolet, therapeutic EMR is emitted to sterilize at least a portion of the EMR conduction system outside the patient's body.

20. The method of claim 17 wherein the radial emission of the non-ultraviolet, therapeutic EMR delivered onto the catheter comprises inhibiting device-related biofilm growth.

* * * * *